(12) United States Patent
Flynn et al.

(10) Patent No.: US 8,193,393 B2
(45) Date of Patent: Jun. 5, 2012

(54) FLUOROETHER DIKETONES FOR HIGH TEMPERATURE HEAT TRANSFER

(75) Inventors: Richard M. Flynn, Mahtomedi, MN (US); Michael G. Costello, Afton, MN (US); Michael J. Bulinski, Houlton, WI (US); Daniel R. Vitcak, Cottage Grove, MN (US); Phillip E. Tuma, Faribault, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 174 days.

(21) Appl. No.: 12/732,688

(22) Filed: Mar. 26, 2010

(65) Prior Publication Data

US 2011/0232871 A1  Sep. 29, 2011

(51) Int. Cl.
C07C 49/173 (2006.01)
C07C 43/00 (2006.01)
C01M 107/34 (2006.01)
C09K 5/04 (2006.01)

(52) U.S. Cl. ........ 568/413; 568/416; 568/674; 568/679; 508/579; 508/582; 252/67

(58) Field of Classification Search .................. 568/413, 568/416, 674, 675; 508/579, 582
See application file for complete search history.

(56) References Cited

U.S. PATENT DOCUMENTS

| | | | |
|---|---|---|---|
| 2,713,593 | A | 7/1955 | Brice |
| 3,699,145 | A | 10/1972 | Sianesi et al. |
| 4,067,884 | A | 1/1978 | Martini |
| 4,136,121 | A | 1/1979 | Martini |
| 5,210,238 | A | 5/1993 | Anderson |
| 5,962,390 | A | 10/1999 | Flynn |
| 6,374,907 | B1 * | 4/2002 | Tousignant et al. ......... 165/80.4 |
| 6,953,082 | B2 | 10/2005 | Costello |
| 7,128,133 | B2 | 10/2006 | Costello |
| 7,385,089 | B2 | 6/2008 | Costello |
| 7,390,427 | B2 | 6/2008 | Costello |
| 2007/0267464 | A1 | 11/2007 | Vitcak |
| 2008/0139683 | A1 | 6/2008 | Flynn |
| 2009/0183856 | A1 | 7/2009 | Bulinski |
| 2010/0108934 | A1 | 5/2010 | Flynn |
| 2010/0263885 | A1 | 10/2010 | Tuma |

FOREIGN PATENT DOCUMENTS

| | | |
|---|---|---|
| EP | 0 557 167 A1 | 8/1993 |
| JP | 2005 126480 A | 5/2005 |
| WO | WO 2007/136948 | 11/2007 |

OTHER PUBLICATIONS

Tasaki, "Solvent Decompositions and Physical Properties of Decomposition Compounds in Li-Ion Battery Electrolytes Studies by DFT Calculations and Molecular Dynamics Simulations," *J. Phys. Chem. B*, 109 pp. 2920-2933, (2005).

Banks, Preparation, Properties and Industrial Applications of Organofluorine Compounds, pp. 19-43, Halsted Press, New York, 1982.

EPA-430-R-06-901, "Uses and Emissions of Liquid PFC Heat Transfer Fluids From the Electronics Sector", pp. 1-37, Jul. 2006.

Marchionni, "The comparison of thermal stability of some hydrofluoroethers and hydrofluoropolyethers", *Journal of Fluorine Chemistry*, 125, 2004, pp. 1081-1086.

U.S. Appl. No. 12/571542, entitled "Appartus Including Hydrofluoroether with High Temperature Stability and Uses Thereof", filed Oct. 1, 2009.

Zapevalova et al., "Synthesis and Reactions of Oxygen-Containing Organofluorine Compounds. IV. Fluorides of Oxygen-Containing Perfluorinated Keto Acids", *Journal of Organic Chemistry of the USSR*, 13, pp. 909-911, Jan. 1, 1977.

International Search Report for PCT/US2011/028932, pp. 3, Jun. 9, 2011.

\* cited by examiner

*Primary Examiner* — Sikarl Witherspoon
(74) *Attorney, Agent, or Firm* — Stephen F. Wolf

(57) ABSTRACT

Fluoroether diketones are provided that can be useful in apparatuses that includes a device and a mechanism for transferring heat. The provided fluoroether diketones are stable at temperatures above 175° C., are environmentally friendly, and are economical to produce. The provided apparatuses can be useful for vapor phase soldering of electronic devices.

16 Claims, No Drawings

FLUOROETHER DIKETONES FOR HIGH TEMPERATURE HEAT TRANSFER

FIELD

This disclosure relates to apparatuses and methods that include fluoroether diketones as a heat-transfer fluid.

BACKGROUND

Presently various fluids are used for heat transfer. The suitability of the heat-transfer fluid depends upon the application process. For example, some electronic applications require a heat-transfer fluid which is inert, has a high dielectric strength, has low toxicity, good environmental properties, and good heat transfer properties over a wide temperature range. Other applications require precise temperature control and thus the heat-transfer fluid is required to be a single phase over the entire process temperature range and the heat-transfer fluid properties are required to be predictable, i.e., the composition remains relatively constant so that the viscosity, boiling point, etc. can be predicted so that a precise temperature can be maintained and so that the equipment can be appropriately designed.

Perfluorocarbons, perfluoropolyethers (PFPEs), and some hydrofluoroethers have been used for heat-transfer. Perfluorocarbons (PFCs) can have high dielectric strength and high resistivity. PFCs can be non-flammable and are generally mechanically compatible with materials of construction, exhibiting limited solvency. Additionally, PFCs generally exhibit low toxicity and good operator friendliness. PFCs can be manufactured in such a way as to yield a product that has a narrow molecular weight distribution. PFCs and PFPEs can exhibit one important disadvantage, however, and that is long environmental persistence which can give rise to high global warming potentials.

Perfluoropolyethers (PFPEs) exhibit many of the same advantageous attributes described for PFCs. In addition, the methods developed for manufacturing these materials can yield products that are not of consistent molecular weight and thus can be subject to performance variability.

SUMMARY

There continues to be a need for heat transfer fluids which are suitable for the high temperature needs of the marketplace such as, for example, for use in vapor phase soldering. There is also a continuing need for heat transfer fluids that have thermal stability at the temperature of use and that have a short atmospheric lifetime so that they have a reduced global warming potential. The provided fluoroether diketones are easy to manufacture, perform well as heat transfer fluids at high temperature, and yield products that can be consistently made. Additionally, they can be thermally stable at use temperatures, typically above 170° C., and have relatively shorter atmospheric lifetimes than conventional materials. There is also a need for apparatuses and processes for high temperature heat transfer that include these fluoroether diketones.

In this disclosure:

"in-chain heteroatom" refers to an atom other than carbon (for example, oxygen and nitrogen) that is bonded to carbon atoms in a carbon chain so as to form a carbon-heteroatom-carbon chain;

"device" refers to an object or contrivance which is heated, cooled, or maintained at a predetermined temperature;

"perfluoroalkylcarbonyl" refers to a moiety that includes a perfluoroalkyl substituent on a carbonyl group;

"inert" refers to chemical compositions that are generally not chemically reactive under normal conditions of use;

"mechanism" refers to a system of parts or a mechanical appliance and can include a heat transfer fluid; and "perfluoro-" (for example, in reference to a group or moiety, such as in the case of "perfluoroalkylene" or "perfluoroalkylcarbonyl" or "perfluorinated") means completely fluorinated such that, except as may be otherwise indicated, there are no carbon-bonded hydrogen atoms replaceable with fluorine; and "terminal" refers to a moiety or chemical group that is at the end of a molecule or has only one group attached to it.

In one aspect, a fluoroether diketone is provided that includes two terminal, branched perfluoroalkylcarbonyl groups that, optionally, comprise at least one in-chain divalent oxygen atom; and an intervening linear, branched or cyclic perfluoroalkylene segment having 4 or more in-chain atoms, said perfluoroalkylene segment containing one or more in-chain divalent oxygen atoms with the proviso that the intervening linear, branched or cyclic perfluoroalkylene segment does not contain the group —$OC_2F_4O$—, wherein the branching of said terminal, branched perfluoroalkylcarbonyl groups is at the carbon atom of said perfluoroalkylcarbonyl group's perfluoroalkyl moiety that is adjacent to said perfluoroalkylcarbonyl group's carbonyl moiety and wherein the total number of carbon atoms in the compound is at least twelve. Typically, the provided fluoroether diketones can have a boiling point at ambient pressure of 170° C. or greater.

In another aspect, an apparatus for heat transfer is provided that includes a device; and a mechanism for transferring heat to or from the device, the mechanism comprising a heat transfer fluid that includes a fluoroether diketone that includes two terminal, branched perfluoroalkylcarbonyl groups that, optionally, comprise at least one in-chain divalent oxygen atom; and an intervening linear, branched or cyclic perfluoroalkylene segment having 4 or more in-chain atoms, said perfluoroalkylene segment containing one or more in-chain divalent oxygen atoms with the proviso that the intervening linear, branched or cyclic perfluoroalkylene segment does not contain the group —$OC_2F_4O$—, wherein the branching of said terminal, branched perfluoroalkylcarbonyl groups is at the carbon atom of said perfluoroalkylcarbonyl group's perfluoroalkyl moiety that is adjacent to said perfluoroalkylcarbonyl group's carbonyl moiety and wherein the total number of carbon atoms in the compound is at least twelve. The device can be an electronic component. The mechanism transfers heat to or from the device and includes a fluoroether diketone. The apparatus can be used, for example for vapor phase soldering of electronic components.

Finally, in another aspect, a method of transferring heat is provided that includes providing a device and transferring heat to or from the device using a mechanism, the mechanism comprising: a heat transfer fluid, wherein the heat transfer fluid includes a fluoroether ketone comprising two terminal, branched perfluoroalkylcarbonyl groups that, optionally, comprise at least one in-chain divalent oxygen atom; and an intervening linear, branched or cyclic perfluoroalkylene segment having 4 or more in-chain atoms, said perfluoroalkylene segment containing one or more in-chain divalent oxygen atoms with the proviso that the intervening linear, branched or cyclic perfluoroalkylene segment does not contain the group —$OC_2F_4O$—, wherein the branching of said terminal, branched perfluoroalkylcarbonyl groups is at the carbon atom of said perfluoroalkylcarbonyl group's perfluoroalkyl moiety that is adjacent to said perfluoroalkylcarbonyl group's carbonyl moiety and wherein the total number of carbon atoms in the compound is at least twelve.

The provided fluoroether diketones can be useful in heat transfer fluids. The provided fluoroether diketones have surprisingly good thermal stability. They also have high specific heat capacity over a wide range of temperatures, high dielectric strength, low electrical conductivity, chemical inertness, and good environmental properties. The provided fluoroether diketones can also be useful as components in vapor phase soldering.

The above summary is not intended to describe each disclosed embodiment of every implementation of the present invention. The detailed description which follows more particularly exemplifies illustrative embodiments.

DETAILED DESCRIPTION

In the following description, it is to be understood that other embodiments are contemplated and may be made without departing from the scope or spirit of the present invention. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range. There continues to be a need for heat transfer fluids which are especially suitable for the high temperature needs of the marketplace such as for example in vapor phase soldering. In such an application temperatures of between 170° C. and 250° C. are typically used with 200° C. being particularly useful for soldering applications using a lead based solder and 230° C. useful for the higher melting lead free solders. At present the materials used in this application are of the perfluoropolyether class. In the past, certain perfluorinated amines for this application area have been marketed. Perfluoropolyethers, while having the required thermal stability at the temperatures employed, also have as a drawback that they are very environmentally persistent with extremely long atmospheric lifetimes and concomitant high global warming potentials due to their high fluorine content. As such there is a need for new materials which have a much shorter atmospheric lifetime and yet still possess sufficient stability to be useful in vapor phase soldering as well as in other high temperature heat transfer applications.

Some hydrofluoroethers have been disclosed as heat-transfer fluids. Exemplary hydrofluoroethers can be found in U.S. Pat. No. 7,988,877 (Flynn et al.), and in U.S. Pat. Publ. Nos. 2007/0267464 (Vitcak et al.) and 2008/0139683 (Flynn et al.), and U.S. Pat. Nos. 7,128,133 and 7,390,427 (Costello et al.). However, the need exists for a heat-transfer fluid which is inert, has high dielectric strength, low electrical conductivity, chemical inertness, thermal stability and effective heat transfer, is liquid over a wide temperature range, has good heat-transfer properties over a wide range of temperatures and also has a reasonably short atmospheric lifetime so that its global warming potential is relatively low.

Perfluorinated diketones of suitable structure, having boiling points of at least 170° C., are believed to possess the required stability as well as the necessary short atmospheric lifetime and hence low global warming potential to make them viable candidates for these high temperature heat transfer applications. For example, a low molecular weight ketone, $C_2F_5COCF(CF_3)_2$ is available as NOVEC 649 from 3M Company, St. Paul, Minn. and is photochemically active in the lower atmosphere and has an atmospheric lifetime of about 5 days. Higher molecular weight perfluorinated diketones would be expected to have a similar absorption in the UV spectrum leading to a similar photochemical lifetime with only slight changes expected due to their structure.

Provided fluoroether diketones include two terminal, branched perfluoroalkylcarbonyl groups that, optionally, comprise at least one in-chain divalent oxygen atom; and an intervening linear, branched or cyclic perfluoroalkylene segment having 4 or more in-chain atoms, said perfluoroalkylene segment containing one or more in-chain divalent oxygen atoms with the proviso that the intervening linear, branched or cyclic perfluoroalkylene segment does not contain the group $—OC_2F_4O—$, wherein the branching of said terminal, branched perfluoroalkylcarbonyl groups is at the carbon atom of said perfluoroalkylcarbonyl group's perfluoroalkyl moiety that is adjacent to said perfluoroalkylcarbonyl group's carbonyl moiety and wherein the total number of carbon atoms in the compound is at least twelve. The number of carbon atoms in the compound can be as high as 30, as high as 24, as high as 18, or even as high as 16. Branched perfluoroalkylcarbonyl groups have alkyl groups that include 3 or more carbon or oxygen atoms and may have as many as 6, as many as 9, as many as 12, or even as many as 24. Examples of branched perfluoroalkyl carbonyl groups include $(CF_3)_2CFCO—$, $C_3F_7OCF(CF_3)CO—$ and $C_4F_9OCF(CF_3)CF_2OCF(CF_3)CO—$. The perfluoroalkylcarbonyl groups are perfluorinated in which substantially all of the carbon-hydrogen bonds of the parent alkyl group or parent alkyl substituents are replaced with carbon-fluorine bonds.

The perfluoroalkylene segment can include, in some embodiments $CF_2CF_2OCF_2CF_2—$, $CF(CF_3)C_2F_4OCF(CF_3)—$, $CF(CF_3)OC_4F_8OCF(CF_3)—$, $C_3F_6OCF(CF_3)—$, $C_3F_6OCF(CF_3)CF_2OCF(CF_3)—$, and $—CF_2CF_2CF_2OCF_2CF_2CF_2—$.

In some embodiments, the provided diketones are symmetrical molecules of the A-B-A structure where A is the perfluoroalkylcarbonyl group and B is the perfluoroalkylene segment. The provided fluoroether diketones have the chemical structure according to formula (I):

$$Rf_1\text{-}C(O)CF(Rf_2)(O)_aRf_3(O)_bCF(Rf_4)C(O)Rf_1 \quad (I)$$

wherein "C(O)" represents a carbonyl group, $Rf_1$ is a perfluoroalkyl group that is branched, cyclic, or a combination thereof, that optionally contains at least one in-chain oxygen or nitrogen heteroatom, $Rf_2$ and $Rf_4$=—F or —$CF_3$, $Rf_3$=a perfluoroalkyl moiety which may be linear, branched, or cyclic having from 2 to 9 carbon atoms which may be interrupted by at most one in-chain divalent ether oxygen atom, at least one of $Rf_2$ or $Rf_4$ is $CF_3$, a and b are independently 0 or 1 and a+b>=1, with the proviso that there is no —$OCF_2CF_2O$— group. Exemplary $Rf_1$ groups include perfluoroisopropyl and derivatives of perfluorinated alkyl groups such as $C_3F_7OCF(CF_3)—$, $C_3F_7OCF(CF_3)CF_2OCF(CF_3)—$,  and $C_4F_9OCF(CF_3)—$.

In some embodiments, the provided fluoroether diketones include:

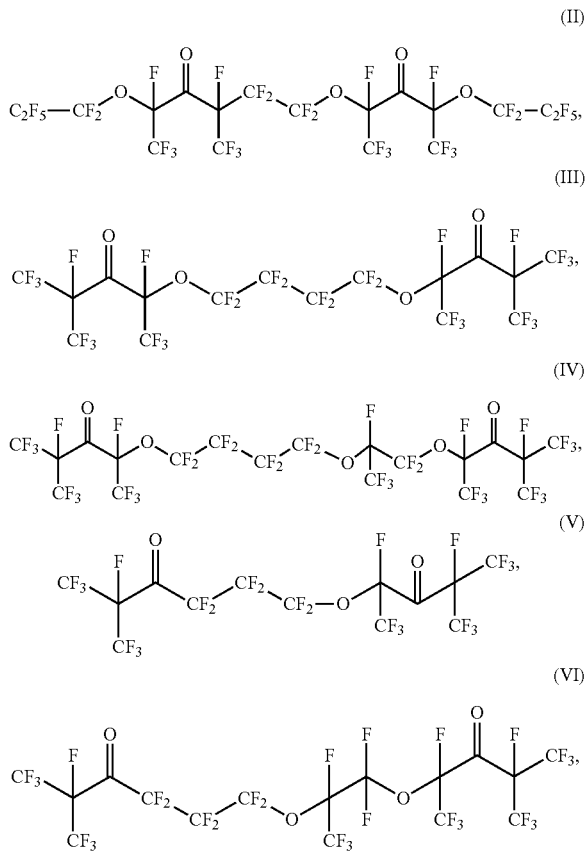

and combinations thereof.

In some embodiments, an apparatus is provided that requires heat transfer. The apparatus includes a device and a mechanism for transferring heat to or from the device using a heat-transfer fluid. The heat-transfer fluid can be a fluoroether ketone as described above. Exemplary apparatuses include refrigeration systems, cooling systems, testing equipment, and machining equipment. Other examples include test heads used in automated test equipment for testing the performance of semiconductor dice; wafer chucks used to hold silicon wafers in ashers, steppers, etchers, PECVD tools; constant temperature baths, and thermal shock test baths. In yet other embodiments, the provided apparatus can include, a refrigerated transport vehicle, a heat pump, a supermarket food cooler, a commercial display case, a storage warehouse refrigeration system, a geothermal heating system, a solar heating system, an organic Rankine cycle device, and combinations thereof.

In certain embodiments, the provided apparatus includes a device. The device is defined herein as a component, workpiece, assembly, etc. to be cooled, heated or maintained at a selected temperature. Such devices include electrical components, mechanical components and optical components. Examples of devices of the present invention include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, and electrochemical cells. In some embodiments, the device can include a chiller, a heater, or a combination thereof. In other embodiments, the device can include an electronic component to be soldered and solder. Typically, the heat required for soldering can be supplied by a vapor phase that has a temperature of greater than 170° C., greater than 200° C., greater than 230° C., or even greater.

In certain embodiments, the present disclosure includes a mechanism for transferring heat. Heat is transferred by placing the heat transfer mechanism in thermal contact with the device. The heat transfer mechanism, when placed in thermal contact with the device, removes heat from the device or provides heat to the device, or maintains the device at a selected temperature. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in PECVD tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even higher.

The heat transfer mechanism includes the provided heat-transfer fluid. The provided heat transfer fluid can be represented by the chemical structure according to formula (I):

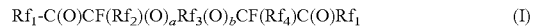

wherein "C(O)" represents a carbonyl group, $Rf_1$ is a perfluoroalkyl group that is branched, cyclic, or a combination thereof, that, optionally, contains at least one in-chain oxygen or nitrogen heteroatom, $Rf_2$ and $Rf_4$=—F or —$CF_3$, $Rf_3$=a perfluoroalkylene moiety which may be linear, branched, or cyclic having from 2 to 9 carbon atoms which may be interrupted by at most one in-chain divalent ether oxygen atom, at least one of $Rf_2$ or $Rf_4$ is $CF_3$—, a and b are independently 0 or 1 and a+b>=1, with the proviso that there is no —$OCF_2CF_2O$— group.

The provided apparatuses and heat transfer fluids fulfill a market need for a high temperature heat transfer fluid. The provided fluoroether diketones provide a stable, high temperature heat transfer fluid.

In one embodiment, the devices can include equipment that is used to test the performance of semiconductor dice. The dice are the individual "chips" that are cut from a wafer of semiconductor substrate. The dice come from the semiconductor foundry and must be checked to ensure they meet functionality requirements and processor speed requirements. The test is used to sort "known good dice" (KGD) from dice that do not meet the performance requirements. This testing is generally performed at temperatures ranging from about −80° C. to about 100° C.

In some cases, the dice are tested one-by-one, and an individual die is held in a chuck. This chuck provides, as part of its design, provision for cooling the die. In other cases, several dice are held in the chuck and are tested either sequentially or in parallel. In this situation, the chuck provides cooling for several dice during the test procedure. It may be advantageous to test dice at elevated temperatures to determine their performance characteristics under conditions of elevated temperature. In this case, a heat-transfer fluid which has good cooling properties well above room temperature is advantageous. In some cases, the dice are tested at very low temperatures. For example, complementary metal-oxide semiconductor ("CMOS") devices in particular operate more quickly at lower temperatures. If a piece of automated testing equipment (ATE) employs CMOS devices "on board" as part of its permanent logic hardware, it may be advantageous to maintain the logic hardware at a low temperature.

Therefore, to provide maximum versatility to the ATE, a heat-transfer fluid typically performs well at both low and high temperatures (i.e., typically has good heat transfer properties over a wide temperature range), is inert (i.e., is non-flammable, low in toxicity, non-chemically reactive), has high dielectric strength, has a low environmental impact, and has predictable heat-transfer properties over the entire operating temperature range.

In another embodiment, the devices can include etchers. Etchers can operate over temperatures ranging from about 70° C. to about 150° C. Typically, during etching, a reactive plasma is used to anisotropically etch features into a semiconductor. The semiconductor can include a silicon wafer or include a II-VI or a III-V semiconductor. In some embodiments, the semiconductor materials can include, for example, III-V semiconductor materials such as, for example, GaAs, InP, AlGaAs, GaInAsP, or GaInNAs. In other embodiments, the provided process is useful for etching II-VI semiconductor materials such as, for example, materials that can include cadmium, magnesium, zinc, selenium, tellurium, and combinations thereof. An exemplary II-VI semiconductor material can include CdMgZnSe alloy. Other II-VI semiconductor materials such as CdZnSe, ZnSSe, ZnMgSSe, ZnSe, ZnTe, ZnSeTe, HgCdSe, and HgCdTe can also be etched using the provided process. The semiconductors to be processed are typically kept at a constant temperature. Therefore, the heat-transfer fluid that can have a single phase over the entire temperature range is typically used. Additionally, the heat-transfer fluid typically has predictable performance over the entire range so that the temperature can be precisely maintained.

In other embodiments, the devices can include ashers that operate over temperatures ranging from about 40° C. to about 150° C. Ashers are devices that can remove the photosensitive organic masks made of positive or negative photo resists. These masks are used during etching to provide a pattern on the etched semiconductor.

In some embodiments, the devices can include steppers that can operate over temperatures ranging from about 40° C. to about 80° C. Steppers are an essential part of photolithography that is used in semiconductor manufacturing where reticules needed for manufacturing are produced. Reticules are tools that contain a pattern image that needs to be stepped and repeated using a stepper in order to expose the entire wafer or mask. Reticules are used to produce the patterns of light and shadow needed to expose the photosensitive mask. The film used in the steppers is typically maintained within a temperature window of +/−0.2° C. to maintain good performance of the finished reticule.

In yet other embodiments, the devices can include plasma enhanced chemical vapor deposition (PECVD) chambers that can operate over temperatures ranging from about 50° C. to about 150° C. In the process of PECVD, films of silicon oxide, silicon nitride, and silicon carbide can be grown on a wafer by the chemical reaction initiated in a reagent gas mixture containing silicon and either: 1) oxygen; 2) nitrogen; or 3) carbon. The chuck on which the wafer rests is kept at a uniform, constant temperature at each selected temperature.

In yet other embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low (or non-) flammability and low environmental impact. Good electrical compatibility requires the heat-transfer fluid candidate to exhibit high dielectric strength, high volume resistivity, and poor solvency for polar materials. Additionally, the heat-transfer fluid must exhibit good mechanical compatibility, that is, it must not affect typical materials of construction in an adverse manner.

The provided device is defined herein as a component, work-piece, assembly, etc. to be cooled, heated or maintained at a selected temperature. Such devices include electrical components, mechanical components and optical components. Examples of devices of the present invention include, but are not limited to microprocessors, wafers used to manufacture semiconductor devices, power control semiconductors, electrical distribution switch gear, power transformers, circuit boards, multi-chip modules, packaged and unpackaged semiconductor devices, chemical reactors, fuel cells, and lasers.

The provided apparatus includes a mechanism for transferring heat. Heat is transferred by placing the heat transfer mechanism in thermal contact with the device. The heat transfer mechanism, when placed in thermal contact with the device, removes heat from the device or provides heat to the device, or maintains the device at a selected temperature. The direction of heat flow (from device or to device) is determined by the relative temperature difference between the device and the heat transfer mechanism. The provided apparatus can also include refrigeration systems, cooling systems, testing equipment and machining equipment. In some embodiments, the provided apparatus can be a constant temperature bath or a thermal shock test bath.

The heat transfer mechanism includes a provided heat-transfer fluid. Additionally, the heat transfer mechanism may include facilities for managing the heat-transfer fluid, including, but not limited to: pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in PECVD tools, temperature-controlled test heads for die performance testing, temperature controlled work zones within semiconductor process equipment, thermal shock test bath liquid reservoirs, and constant temperature baths. Constant temperature baths are typically operated over a broad temperature range. Therefore, desirable heat-transfer fluids preferably have a wide liquid range and good low-temperature heat transfer characteristics. A heat-transfer fluid having such properties allows a very wide operating range for the constant temperature bath. Typically, most testing fluids require fluid change-out for wide temperature extremes. Also, good temperature control is essential for accurately predicting physical properties of the heat-transfer fluids.

In other aspects, a method of transferring heat is provided that includes providing a device and transferring heat to or from the device using a mechanism. The mechanism can include a heat transfer fluid such as the fluoroether diketones disclosed herein. The provided method can include vapor phase soldering wherein the device is an electronic component to be soldered.

Objects and advantages of this invention are further illustrated by the following examples, but the particular materials and amounts thereof recited in these examples, as well as other conditions and details, should not be construed to unduly limit this invention

EXAMPLES

Unless otherwise noted, all solvents and reagents may be obtained from Aldrich Chemical Co. of Milwaukee, Wis. As used herein, "NOVEC-7200" refers to ethyl perfluorobutyl ether and is available from 3M Company, St. Paul, Minn. Also as used herein "HFPO" refers to hexafluoropropene oxide and "HFP" refers to hexafluoropropene. "Diglyme" refers to diethylene glycol dimethyl ether.

Example 1

Preparation of 1,1,1,2,4,5,5,6,6-Nonafluoro-2-heptafluoropropyloxy-6-(1,3,4,4,4-pentafluoro-3-heptafluoropropyloxy-2-oxo-1-trifluoromethyl-butoxy)-4-trifluoromethyl-hexan-3-one. (II)

2,2,3-trifluoro-3-trifluoromethyl-butanedioyl difluoride was prepared by electrochemical fluorination of dimethyl itaconate in a Simons ECF cell of essentially the type described in U.S. Pat. No. 2,713,593 (Brice et al.) and in R. E. Banks, *Preparation, Properties and Industrial Applications of Organofluorine Compounds*, pages 19-43, Halsted Press, New York (1982). This diacid fluoride (107.3 g, 0.44 mol), potassium fluoride (5.4 g, 0.093 mol, Aldrich) and diglyme (30 g, Aldrich) were combined in a 600 mL Parr reactor. Hexafluoropropylene oxide (73.75 g, 0.44 mol, DuPont) was added as a gas to the reactor at a rate such that the temperature remained below 12° C. and the pressure remained below 10 psig. Addition of HFPO was complete after two hours. The mix was stirred for one hour after addition. The heterogeneous product solution was then filtered and the lower fluoroether product phase was separated from the diglyme phase. A total of 103.8 g of 2,3,3,4,4-pentafluoro-4-(1,2,2,2-tetrafluoro-1-fluorocarbonyl-ethoxy)-2-trifluoromethyl-butyryl fluoride $FC(O)CF(CF_3)CF_2CF_2OCF(CF_3)C(O)F$ was isolated. 70 grams of the isolated acid fluoride (0.17 mol) was then combined with 1,1,1,2,2,3,3-heptafluoro-3-trifluorovinyloxy-propane (95.7 g, 0.36 mol, Dyneon), cesium fluoride (12.8 g 0.085 mol) and 100 grams of diglyme solvent in a 600 mL Parr reactor. The mix was heated to 75° C. for 24 hours. The reaction mix was then filtered and the lower fluoroether product phase was separated from the solvent. The product was purified by fractional distillation using a concentric tube column. The product mass was verified by GC/MS.

Example 2

Preparation of $(CF_3)_2CFC(O)CF(CF_3)$ $OCF_2CF_2CF_2OCF(CF_3)C(O)CF(CF_3)_2$ (III) and its isomer (VI)

Preparation of Precursor $FOCCF_2CF_2COF$.

Tetrafluorosuccinyl fluoride was prepared from the electrochemical fluorination of butyrolactone in a Simons ECF cell of the type described in U.S. Pat. No. 2,713,593 (Brice et al.) and in R. E. Banks, *Preparation, Properties and Indus-trial Applications of Organofluorine Compounds*, pages 19-43, Halsted Press, New York (1982). Purification by fractional distillation gave material that was 94.3% tetrafluorosuccinyl fluoride and 4.92% perfluorobutyrolactone as determined by GC-FID, GC/MS, $^1$H-NMR and $^{19}$F-NMR analysis.

Preparation of Intermediate $FOCCF(CF_3)$ $OCF_2CF_2CF_2OCF(CF_3)COF$, Isomers and Higher Oligomers.

A clean dry 400 mL stainless steel jacketed Parr pressure reactor was charged with spray-dried potassium fluoride (1.6 g) and anhydrous diglyme (27 g). The vessel was sealed and cooled using an FTS Systems refrigerated circulation bath set at minus 25° C. Tetrafluorosuccinyl fluoride (191.5 g) was added to the sealed reactor as a liquid from a charge cylinder. The refrigerated circulating bath was set at 16° C. during the eight hour addition of HFPO (314 g). The temperature of the reaction during the addition ranged from ~18-21° C. The reaction was held at ambient temperature for 16 hours after which the refrigeration unit was turned back on and the reactor cooled to 16° C. and the remainder of the HFPO (53.2 g) was added over 2.5 hours. Following a one hour reaction and one hour hold time during which the phases were allowed to separate, the lower HFPO tetrafluorosuccinyl fluoride adduct phase was drained (530 g). GC and GC/MS analysis showed the following components.

| Material | GC Area % |
|---|---|
| 1-1 HFPO tetrafluorosuccinyl fluoride adducts | 4.15 |
| 2-1 HFPO symmetrical tetrafluorosuccinyl fluoride adducts | 47.61 |
| 2-1 HFPO unsymmetrical tetrafluorosuccinyl fluoride adducts | 16.68 |
| 3-1 HFPO tetrafluorosuccinyl fluoride adducts | 19.90 |
| 4-1 HFPO tetrafluorosuccinyl fluoride adducts | 6.00 |
| Other compounds | 5.66 |

Preparation of $(CF_3)_2CFC(O)CF(CF_3)$ $OCF_2CF_2CF_2OCF(CF_3)C(O)CF(CF_3)_2$ and its Isomer. (III) and (VI)

A clean, dry, 600 mL stainless steel Parr pressure reactor was charged with spray-dried potassium fluoride (13 g), anhydrous diglyme (156 g), NOVEC-7200 (185.6 g) and the HFPO tetrafluorosuccinyl fluoride adducts (105 g). The vessel was sealed and heated to 75° C. HFP (73.8 g) was added over five hours and reacted for 16 hours. A second charge of HFP (40.6 g) was added over an additional three hours and the reaction was completed following a 3 hour hold. The mixture was cooled to room temperature and transferred to a 1 liter round bottom flask set up for a 40 mm Hg vacuum one-plate distillation. The mixture was heated to 75° C. to remove NOVEC-7200. The flask contents was cooled to ambient temperature and transferred to a 500 mL reparatory funnel. After about an hour the lower fluoroether phase was separated and washed one time with about an equal volume of 2N HCl solution to recover the lower fluoroether phase, 145 grams. Two isomers of the desired materials were obtained in a purity of 50.9% as determined by GC-FID and GC/MS analysis. Other diketones corresponding to the various HFPO tetrafluorosuccinyl fluoride adducts comprised the remaining material. The diketone isomeric mixture was further purified by distillation and the composition confirmed by GC-FID, GC/MS, $^1$H-NMR and $^{19}$F-NMR analysis to contain the following two isomers with a boiling point of 211.6° C. $(CF_3)_2CFC(O)CF(CF_3)OCF_2CF_2CF_2OCF(CF_3)C(O)$ $CF(CF_3)_2$ ~74.9%

$(CF_3)_2CFC(O)CF_2CF_2CF_2OCF(CF_3)CF_2OCF(CF_3)C(O)$
$CF(CF_3)_2$ ~20.9%

Example 3

Preparation of $(CF_3)_2CFC(O)CF(CF_3)$
$OCF_2CF_2CF_2OCF(CF_3)CF_2OCF(CF_3)C(O)CF$
$(CF_3)_2$ (IV)

Refractionation of the higher boiling fraction from the reaction mixture of Example 2 afforded 30 grams of diketone derived from the 3-1 HFPO tetrafluorosuccinyl fluoride adducts and which contained ~96.1% of the 3-1 diketone as determined by GC and GC/MS analysis; boiling point was approximately 243° C.

Example 4

Preparation of $(CF_3)_2CFC(O)CF_2CF_2CF_2OCF(CF_3)$
$C(O)CF(CF_3)_2$ (V)

A clean dry 600 mL stainless steel Parr pressure reactor was charged with cesium fluoride (6 g) and anhydrous diglyme (20 g). The vessel was sealed and cooled using an FTS Systems refrigerated circulation bath set at minus 25° C. Tetrafluorosuccinyl fluoride (95.4 g, 81.3% purity) was added to the reactor from a charge cylinder. The refrigerated circulating bath was set at minus 11° C. during the nineteen hour addition of hexafluoropropene oxide (73.8 g). The reactor was then heated to 80° C. and hexafluoropropene (153 g) was added over twenty four hours. The reactor contents were cooled to ambient temperature and transferred to a 500 mL reparatory funnel. The lower fluoroether phase was fractionated to yield 24 grams containing 96.4% of the desired material as determined by GC-FID and GC/MS analysis.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows. All references cited in this disclosure are herein incorporated by reference in their entirety.

What is claimed is:

1. A compound having the formula, $Rf_1\text{-}C(O)CF(Rf_2)(O)_aRf_3(O)_bCF(Rf_4)C(O)Rf_1,$ wherein $Rf_1$=a perfluoroalkyl group that is branched, cyclic, or a combination thereof, that, optionally, contains at least one in-chain oxygen or nitrogen heteroatom, $Rf_2$ and $Rf_4$=—F or —$CF_3$, $Rf_3$=a perfluoroalkylene moiety which may be linear, branched or cyclic having from 4 to 9 carbon atoms which may be interrupted by at most one in-chain divalent ether oxygen atom at least one of $Rf_2$ or $Rf_4$ is $CF_3$—, a and b are independently 0 or 1 and a+b≧1, with the proviso that $Rf_3$ does not contain —$OCF_2CF_2O$—.

2. A fluorodiketone selected from the group consisting of

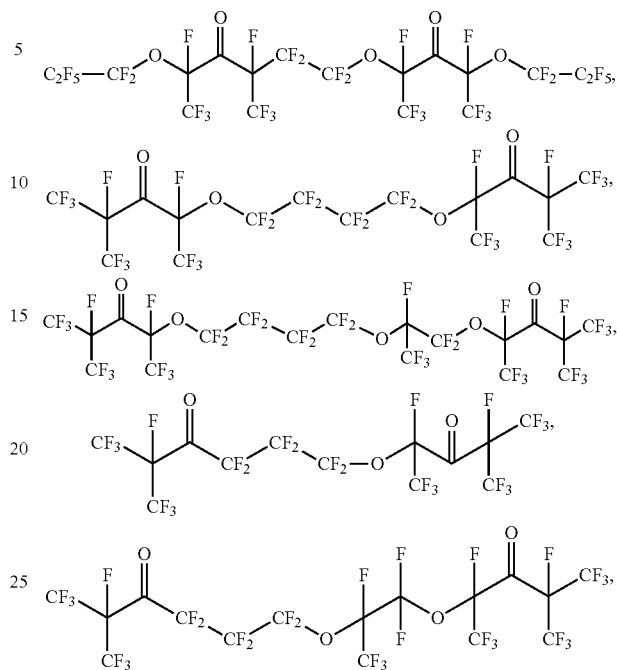

and combinations thereof.

3. An apparatus for heat transfer comprising:
a device; and
a mechanism for transferring heat to or from the device, the mechanism comprising a heat transfer fluid that includes a fluoroether diketone comprising:
a compound having the formula, $Rf_1\text{-}C(O)CF(Rf_2)(O)_aRf_3(O)_bCF(Rf_4)C(O)Rf_1,$ wherein $Rf_1$=a perfluoroalkyl group that is branched, cyclic, or a combination thereof, that, optionally, contains at least one in-chain oxygen or nitrogen heteroatom, $Rf_2$ and $Rf_4$=—F or —$CF_3$, $Rf_3$=a perfluoroalkylene moiety which may be linear, branched or cyclic having from 4 to 9 carbon atoms which may be interrupted by at most one in-chain divalent ether oxygen atom at least one of $Rf_2$ or $Rf_4$ is $CF_3$—, a and b are independently 0 or 1 and a+b≧1, with the proviso that $Rf_3$ does not contain —$OCF_2CF_2O$—.

4. An apparatus according to claim 3, wherein the device is selected from a microprocessor, a semiconductor wafer used to manufacture a semiconductor device, a power control semiconductor, an electrochemical cell (including a lithium-ion cell), an electrical distribution switch gear, a power transformer, a circuit board, a multi-chip module, a packaged or unpackaged semiconductor device, a fuel cell, and a laser.

5. An apparatus according to claim 3, wherein the mechanism transfers heat to the device.

6. An apparatus according to claim 3, wherein the mechanism transfers heat from the device.

7. An apparatus according to claim 3 wherein the mechanism maintains the device at a selected temperature.

8. An apparatus according to claim 3, wherein the mechanism for transferring heat is a component in a system for cooling the device, wherein the system is selected from a system for cooling wafer chucks in PECVD tools, a system for controlling temperature in test heads for die performance testing, a system for controlling temperatures within semiconductor process equipment, a thermal shock testing of an electronic device, and a system for maintaining a constant temperature of an electronic device.

9. An apparatus according to claim 3 wherein the device comprises an electronic component to be soldered and solder.

10. An apparatus according to claim 9, wherein the mechanism comprises vapor phase soldering.

11. A method of transferring heat comprising:
providing a device; and
transferring heat to or from the device using a mechanism, the mechanism comprising:
a heat transfer fluid,
wherein the heat transfer fluid includes a fluoroether diketone comprising:
a compound having the formula, $Rf_1-C(O)CF(Rf_2)(O)_aRf_3(O)_bCF(Rf_4)C(O)Rf_1$, wherein $Rf_1$=a perfluoroalkyl group that is branched, cyclic, or a combination thereof, that, optionally, contains at least one in-chain oxygen or nitrogen heteroatom,
$Rf_2$ and $Rf_4$=—F or —$CF_3$,
$Rf_3$=a perfluoroalkylene moiety which may be linear, branched or cyclic having from 4 to 9 carbon atoms which may be interrupted by at most one in-chain divalent ether oxygen atom at least one of $Rf_2$ or $Rf_4$ is $CF_3$—,
a and b are independently 0 or 1 and a+b≧1, with the proviso that $Rf_3$ does not contain —$OCF_2CF_2O$—.

12. A method of transferring heat according to claim 11, wherein the device is an electronic component to be soldered.

13. An apparatus for heat transfer comprising:
a device; and
a mechanism for transferring heat to or from the device, the mechanism comprising a heat transfer fluid that includes a fluoroether diketone according to claim 2.

14. An apparatus for heat transfer according to claim 13, wherein the fluoroether diketone has a boiling point of greater than 200° C. at ambient pressure.

15. A method of transferring heat comprising:
providing a device; and
transferring heat to or from the device using a mechanism, the mechanism comprising:
a heat transfer fluid,
wherein the heat transfer fluid includes a fluoroether diketone according to claim 2.

16. A method of transferring heat according to claim 15, wherein the fluoroether diketone has a boiling point of greater than 200° C. at ambient pressure.

* * * * *

UNITED STATES PATENT AND TRADEMARK OFFICE
CERTIFICATE OF CORRECTION

| | | |
|---|---|---|
| PATENT NO. | : 8,193,393 B2 | Page 1 of 1 |
| APPLICATION NO. | : 12/732688 | |
| DATED | : June 5, 2012 | |
| INVENTOR(S) | : Richard Mark Flynn | |

It is certified that error appears in the above-identified patent and that said Letters Patent is hereby corrected as shown below:

<u>Column 3,</u>
Line 32, start a new paragraph at the word "There".

<u>Column 10,</u>
Line 54, delete "reparatory" and insert --separatory-- therefor.

<u>Column 11,</u>
Line 36, delete "reparatory" and insert --separatory-- therefor.

Signed and Sealed this
Twenty-seventh Day of November, 2012

David J. Kappos
*Director of the United States Patent and Trademark Office*